United States Patent
Westermann et al.

(10) Patent No.: US 6,933,385 B2
(45) Date of Patent: Aug. 23, 2005

(54) PROTECTED 3,5-DIHYDROXY-2,2-DIMETHYL-VALEROAMIDES FOR THE SYNTHESIS OF EPOTHILONES AND DERIVATIVES AND PROCESS FOR THE PRODUCTION AND THE USE

(75) Inventors: Jurgen Westermann, Berlin (DE); Johannes Platzek, Berlin (DE); Orlin Petrov, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/211,242

(22) Filed: Aug. 5, 2002

(65) Prior Publication Data

US 2003/0158412 A1 Aug. 21, 2003

Related U.S. Application Data

(60) Provisional application No. 60/313,015, filed on Aug. 20, 2001.

(30) Foreign Application Priority Data

Aug. 3, 2001 (DE) .......................................... 101 38 348

(51) Int. Cl.$^7$ ..................... C07D 265/30; C07D 211/06; C07D 207/04

(52) U.S. Cl. ........................ 544/106; 548/406; 548/530; 546/184; 546/248; 549/356; 549/357; 549/369; 549/375

(58) Field of Search .................................. 544/106, 148, 544/189; 548/406, 530; 546/187, 248; 549/356, 375; 5144/149; 514/231.5

(56) References Cited

FOREIGN PATENT DOCUMENTS

WO    WO 00/58254 A1    10/2000

OTHER PUBLICATIONS

Taylor et al., "Total Synthesis of Epothilones B and D," *Organic Letters*, vol. 3, No. 14, 2001, pp. 2221–2224.

Fürstner et al., "Concise Total Syntheses of Epothilone A and C Based on Alkyne Metathesis," *Chem. Commun.*, 2001, pp. 1057–1059.

Mulzer et al., "Total Syntheses of Epothilones B and D," *J. Org. Chem.*, vol. 65, No. 22, 2000, pp. 7456–7467.

*Primary Examiner*—Golam M M Shameem
(74) *Attorney, Agent, or Firm*—Millen, White, Zelano, Branigan, P.C.

(57) ABSTRACT

The invention relates to new protected 3,5-dihydroxy-2,2-dimethyl-valeroamides for the synthesis of epothilones and derivatives and process for the production and the use of the new compounds for the production of epothilones or epothilone derivatives.

22 Claims, No Drawings

PROTECTED 3,5-DIHYDROXY-2,2-DIMETHYL-VALEROAMIDES FOR THE SYNTHESIS OF EPOTHILONES AND DERIVATIVES AND PROCESS FOR THE PRODUCTION AND THE USE

This application claims the benefit of the filing date of U.S. Provisional Application Ser. No. 60/313,015 filed Aug. 20, 2001.

The invention relates to the subject that is characterized in the claims, i.e., new intermediate products and process for their production and the use. The process for the production of new intermediate products starts from economical starting materials, yields the intermediate products in high enantiomer purities, in high chemical purity, in good yields, and allows the industrial-scale production.

The invention is used in the synthesis of component A from natural and synthetically modified epothilones or derivatives. Epothilones are 16-membered macrolide rings that were isolated from the cultures of Myxobacterium Sorangium Cellosum and are representatives of a class of promising anti-tumor agents that were tested and found to be effective against a number of cancer lines. A survey of the syntheses has been described by J. Mulzer et al. in J. Org. Chem. 2000, 65, 7456–7467.

A-Component fragment

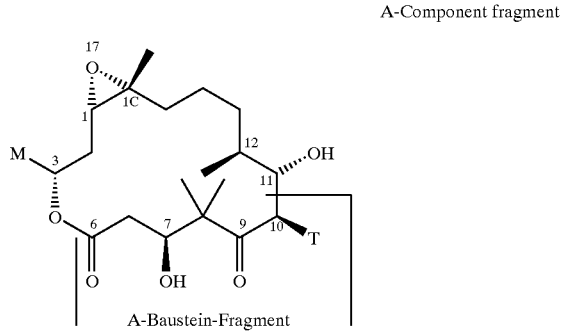

A-Baustein-Fragment

In the literature, in addition to the natural epothilones, a number of synthetic epothilone derivatives are described that vary for the most part within radicals M and T. In most cases, M stands for a heterocyclic radical here. Most syntheses of the natural epothilones and the synthetic epothilone derivatives use the A-component fragment, which represent carbon atoms $C_5$–$C_{10}$ in the macrolide. Within this component A (see below), $C_1$ is the $C_5$ in the macrolide and $C_6$ is the $C_{10}$ in the macrolide, etc.

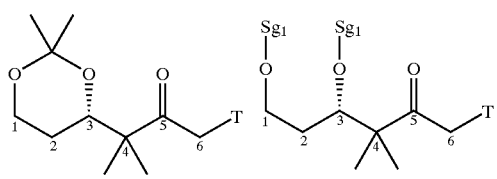

Within the component, T stands for a $C_1$–$C_4$ alkyl or alkenyl radical, and Sg1 and Sg2 stand for the protective groups that are familiar to one skilled in the art, such as, e.g., the TBDMS group.

A possible production of the A-component is described in, for example, WO00/58254 (University of Wisconsin). A synthesis of β-keto esters, which can be converted into multistage sequences in component A, is disclosed therein.

The chirality is introduced by an asymmetric hydrogenation of a β-keto ester according to Noyori:

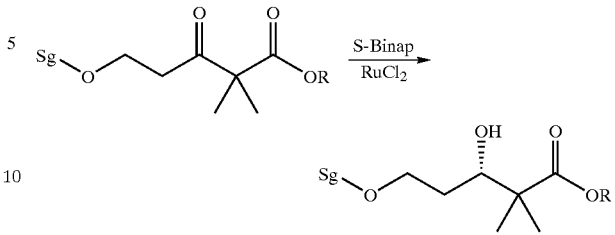

In this connection, the conversion of the ester group into a ketone can only be done by means of a multistage sequence. In this case, after a protection of the 1- and 3-hydroxy group, the ester group (C-5 atom) is reduced to form alcohol, the oxidation to aldehyde is carried out, the Grignard addition of an alkyl radical with an alkylmagnesium or alkyllithium compound yields a secondary alcohol, which then is oxidized. To get from the ester to the ketone, a total of 6 steps are necessary. The direct reaction of an ester is not selective, since the intermediately produced product is further reacted. The following diagram shows the entire synthesis pathway:

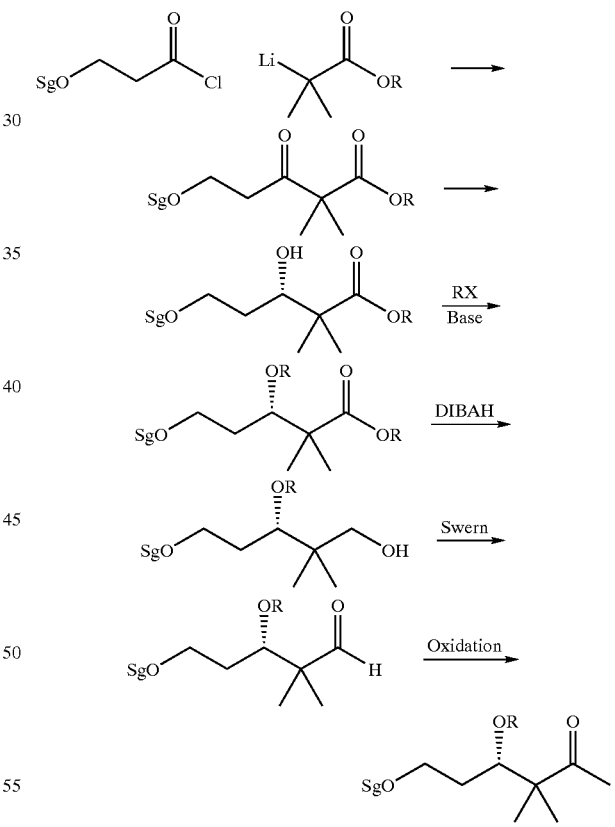

Another method for creating component A is described by B. Paniker et al. in Tetrahedron 2000, 56, 7859–7868. It is described there that the aldol reaction with a chiral component yields a less selective reaction. By the roundabout way of an N-methylthioacetyl-oxazolidinone, the synthesis of the chiral C3 atom in a multistage sequence with improved diastereoselectivity by means of boron enolate is described. To achieve usable diastereoselectivities, a methylthio substitution is necessary; the thio ether is cleaved off after the aldol reaction.

Further, a sequence can be found in the prior art (R. E. Taylor, Y. Chen, Org. Lett. (2001), 3(14), 2221–2224) in which a phenyl ester is used. The yield that is achieved in this case is indicated with 77%. In the example that is described by A. Fürstner in Chem. Comm. 2001, 1057–1059, a 67% yield is achieved. These yields of the methods from the prior art are significantly less than those of this invention.

In J. Org. Chem. 2000, 65, 7456–7467, an asymmetrical synthesis of a β-keto ester is further described, whereby a variant in asymmetrical form is performed as an aldol reaction. In this method, D-Ts-valine is used as a catalyst, which can be produced from the expensive amino acid D-valine. This method yields an ee-value of 90%. An asymmetrical aldol reaction, in which the yield is 71%, is described by R. E. Taylor, Y. Chen, Org. Lett. (2001), 3(14), 2221–2224 as another example in this regard.

Another method for the production of a double TBDMS-protected A-component-ethyl ketone is finally described by Nicolaou in Chem. Eur. J. 2000, 6, 2783–2800.

This invention includes the object of being able to produce a universally usable starting intermediate compound of general formula I as well as the optically pure antipodes of general formulas Ia, Ib,

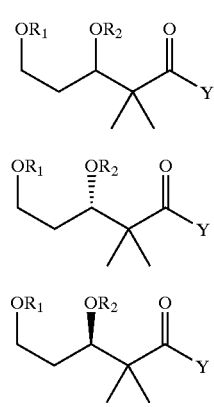

in which R1, R2 can be the same or different and, independently of one another, stand for an alcohol protective group that is familiar to one skilled in the art, for example, benzyl, 4-methoxybenzyl, 3,4-dimethoxybenzyl, THP, TBDMS, TMS, TES, TIP, TBDPS, MEM, MOM, allyl, trityl, or, in the case when R1 and R2 are bridged, stand for a ketal protective group, such as, e.g.,

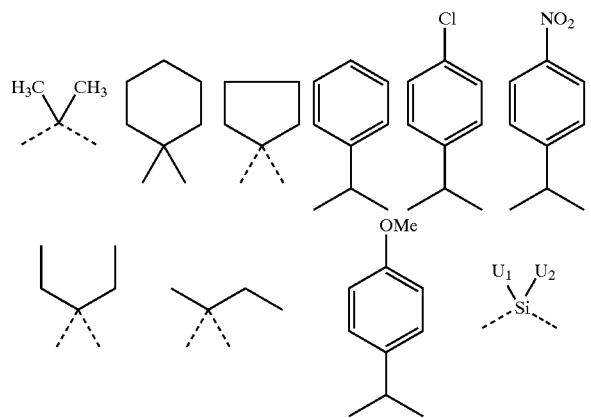

U1, U2:Alkyl, Phenyl, tertbutyl

-continued

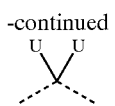

U = C1–C6 Alkyl

Y stands for a group -NA1A2, whereby A1 and A2, independently of one another, stand for the radicals C1–C6 alkyl, such as methyl, ethyl, propyl, or aryl or aralkyl, such as phenyl, benzyl, OH, OMe, O-benzyl or for a radical

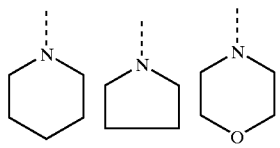

to produce A-component fragments for epothilone total syntheses.

To this end, compounds of general formula I are reacted as described below:

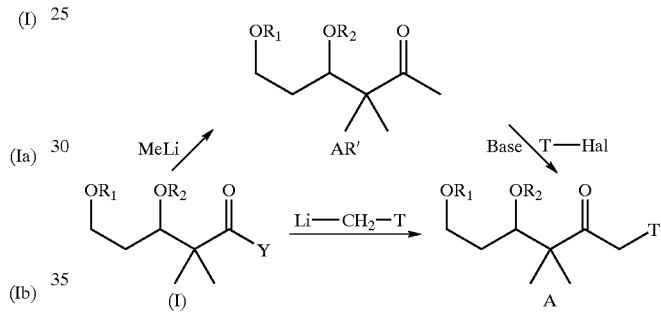

The reactions of the compounds of general formula I, as well as their antipodes Ia, Ib to form ketones AK are carried out with methyllithium or methyl-Grignard compounds according to the standard process that is known to one skilled in the art; the aqueous working-up then yields the ketone. The subsequent alkylation with an alkyl or alkenyl-halide of formula T-Hal (Hal=Cl, Br, I or tosylate, mesylate, triflate, etc.) with the addition of a base yields the A-component fragments.

A can also be directly obtained, however, by the amides of general formula I being reacted directly with organometallic compounds, such as, e.g., the lithium compound Li—CH2-T and then being worked up in aqueous form.

As a rule, the above-described reactions run smoothly and produce the A-components in high yields.

There was therefore a need for an industrial-scale process that allows it to prepare a universally usable intermediate compound for the production of the A-component in the epothilone total synthesis.

In addition to the high yields in the conversion into the A-components, the relatively easy accessibility of the compounds of general formula I from relatively inexpensive starting materials is emphasized. Moreover, the compounds according to the invention are stable in storage in contrast to the esters and ketones that are known in the literature and are, for the most part, crystalline solids and can be purified by crystallization. In this way, high chemical and optical yields (e.e.>98%) can be achieved.

Variant I (General Access via Aldol Reactions)

a) In the case where R1 and R2 stand for a ketal protective group, or R1 =R2, compounds of general formula I can be produced from compounds of general formula II

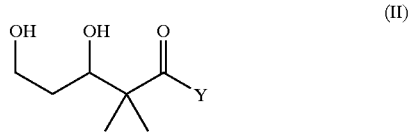
(II)

whereby Y has the above-mentioned meaning,
according to the methods for protective group chemistry that are known to one skilled in the art; thus, for example, their production and cleavage are described by P. J. Kocienski in "Protecting Groups," Georg Thieme Verlag Stuttgart, New York, 1994, as well as in Houben Weyl, 4th Edition, Volume VI/1b, p. 737, Thieme Stuttgart 1984.

b) In the case that R1 and R2 do not represent any ketal-protective group but nevertheless can be the same or different, the production of the compounds of general formula I can be carried out directly from the compounds of general formula III, by protective group R2 being introduced according to methods that are known in the literature (J. Mulzer et al., J. Org. Chem. 2000, 65, 7456–7467).

Compounds of general formula II can be produced from compounds of general formula III

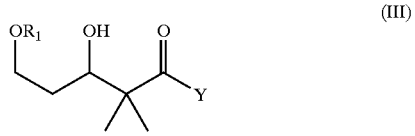
(III)

in which Y stands for the above-indicated meaning, and R1 stands for a protective group in the above-indicated meaning, by cleavage of protective group R1 according to the process, known to one skilled in the art, of the protective group cleavage of alcohols (P. J. Kocienski in "Protecting Groups," Georg Thieme Verlag Stuttgart, New York 1994/ Houben Weyl, 4th Edition Volume VI/1b p. 737, Thieme Stuttgart 1984).

Compounds of general formula III can be produced from compounds of general formula IV

(IV)

by reaction of the compounds of formula V

(V)

in which Y and R1 are in the above-indicated meaning, and L stands for a silyl protective group, such as, e.g., TBDMS, TMS, TES, TIP, TBDPS,
in a way that is known to one skilled in the art by the techniques of aldol condensation. (C. H. Heathcock in Modem Synthesis Methods, 1992 (Editors R. Scheffold, VHCA Basel 1992, pp. 1–102).

The production of compounds of general formula IV are known to one skilled in the art, however:
R1: THP in JOC, 1984, 49, 2301–2309
R1: benzyl in J. Chem. Soc. Perk. Trans 1, 2000, 2429–2454,
R1: TBDMS in JOC, 2000, 65, 7456–7467
The production of compounds of general formula V is novel and is described in the examples.
Variant II (Production of Optically Active Intermediate Products of General Formula Ia)
For the production of optically active compounds of general formula Ia

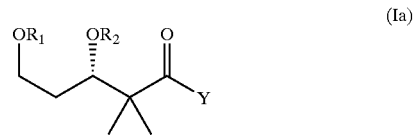
(Ia)

the procedure is analogous to that described under Variant I. Starting from the optically active intermediate stage of general formulas IIa and IIIa

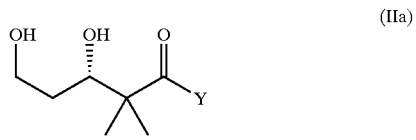
(IIa)

compounds of general formula Ia are produced.
Compounds of general formula IIa are produced analogously from the optically active precursors of general formula IIIa

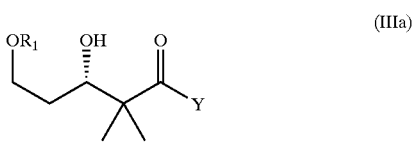
(IIIa)

Optically active compounds of general formula IIIa are accessible as follows:
1. Separation of the racemic compound of general formula III in the chiral phase (Lit.: G. Roussel, P. Pirs, Chirabase, Pure and Applied Chemistry, 1993, 65, 235–244), primarily by SMB technique: (A. Seidel-Morgenstem et al., Chromat. A. 1998, 827/2, 175–191).
2. Starting from the racemic alcohol of general formula III, by esters of general formula VI

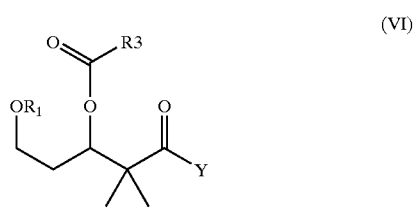
(VI)

in which R3 stands for a $C_1$–$C_6$ alkyl group or an allyl, phenyl or benzyl group, being produced according to the process of esterification that is known to one skilled in the art, and the latter being saponified enantioselectively by enzymatic or microbiological methods. The alcohol that is produced is clearly distinguished in its Rf value from the ester that is used so that the two can easily be separated from another, e.g., by column chromatography.

3. By aldol condensation that is mediated with chiral catalysts, by compounds of general formulas IV and V being reacted with use of a catalytic or stoichiometric amount of a chiral aldol catalyst:

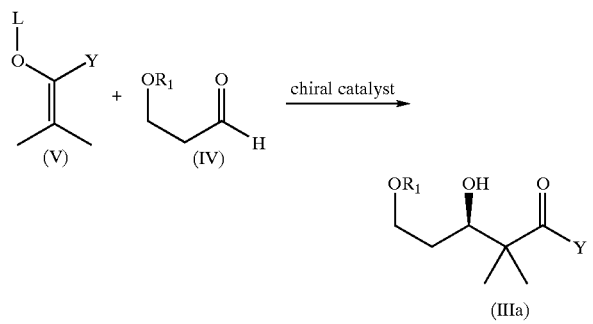

Literature: See, e.g., J. Org. Chem. 2000, 65, 7456–7467.

4. By a chiral reduction of the ketone of general formula VII

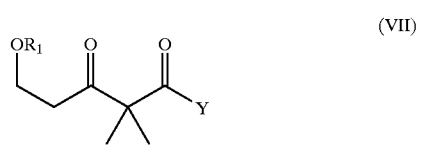

being performed according to methods that are known to one skilled in the art. Lit.: Noyori et al., J. Am. Chem. Soc. 1987, 109, 5850; Noyori et al., J. Am. Chem. Soc. 1988, 110, 629, R. C. Larock in "Comprehensive Organic Transformations," VCH Publishers New York 1989, ISBN 0-89573-710-8, pages 540–548.

Compounds of general formula VII, with R1 and Y in the above-indicated meaning, can be obtained by reaction of the compounds of general formula V with compounds of general formula VIII

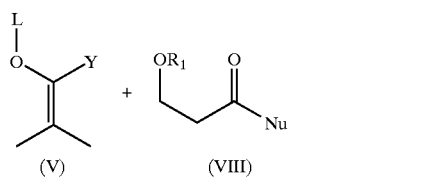

in which Nu stands for a leaving group, such as Cl, Br, imidazole, —OPh, —O—C6H4NO2, —O—C1–C4 alkyl, etc.

The reaction is carried out in a way that is known to one skilled in the art. Lit.: Ann. 1962, 655, 90, R. C. Larock in "Comprehensive Organic Transformations," VCH Publishers New York 1989, ISBN 0-89573-710-8, pages 685–702.

The production of compounds of general formula VIII is described in the literature: J. Med. Chem. 1999, 706–721.

In some cases, it has proven advantageous when compounds of general formula VII are produced by oxidation from the racemic alcohols of general formula II according to the methods of oxidation that are known to one skilled in the art (e.g., Swern oxidation, PDC, PCC, etc.).

In some cases, it has proven advantageous when compounds of general formula V are reacted with propiolactone to form compounds of general formula IX:

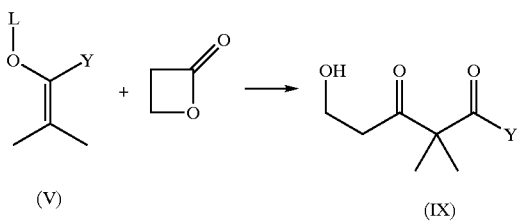

Compounds of general formula IX can be converted very easily into compounds of general formula VII by introducing protective groups according to the methods that are known to one skilled in the art (see: P. J. Kocienski described in "Protecting Groups," Georg Thieme Verlag Stuttgart, New York 1994, as well as in Houben Weyl, 4th Edition, Volume VI/1b, p. 737, Thieme Stuttgart 1984).

Starting from compounds of general formula IX, however, compounds of general formula IIa

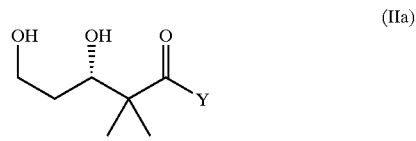

can also be obtained by the keto group being reduced chirally with chemical or microbiological methods (e.g., according to: J. Org. Chem. 1985, 50, 127/J. Chem. Soc., Chem. Commun. 1987, 1368).

Variant III

Compounds of general formula Ia

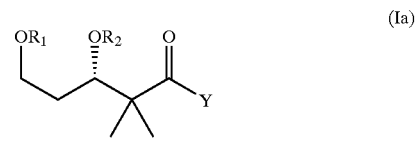

can also be produced by introducing protective groups according to methods that are known in the literature for introducing alcohol protective groups from the compounds of general formula X

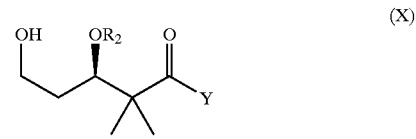

(see literature cited above for introducing protective groups).

Compounds of general formula X can be produced from compounds of general formula XI (XI)

in which R4 stands for a methyl, ethyl or benzyl group, by ester reduction according to methods that are known to one skilled in the art. Lit.: R. C. Larock in "Comprehensive Organic Transformations," VCH Publishers New York 1989, ISBN 0-89573-710-8, pages 549–551).

Compounds of general formula XI can be produced from compounds of general formula XII (XII)

in which R4 stands for a $C_1$–$C_6$ alkyl, methyl, ethyl, tert-butyl, phenyl or benzyl group, by introducing protective group R2 according to methods that are known to one skilled in the art (see above).

Compounds of general formula XII can be obtained from β-keto esters of general formula XIII (XIII)

by methods of chiral reduction (chemical or enzymatic). Lit.: Chemie in unserer Zeit [Chemistry in Our Time], 1996, 30, 201–213, R. C. Larock in "Comprehensive Organic Transformations," VCH Publishers New York 1989, ISBN 0-89573-710-8, pages 540–547).

Compounds of general formula XIII are obtained by reaction of compounds of general formula XIV with compounds of general formula V (XIV)

(V)

Compounds of general formula XIV are known in the literature: Compounds of general formula V are novel, for production see above and the examples, or can also be obtained from the reaction of compounds of general formulas XIIIa and XIIIb.

(XIIIa)    (XIIIb)

(XIII)

Here, Nu is in the meaning of the leaving group that is already mentioned above, and Q stands for a hydrogen atom or a COOH group. If Q is a hydrogen atom, XIIIa is deprotonated with an organic base, such as, e.g., LDA and then is reacted with the activated acid derivative according to the methods that are familiar to one skilled in the art.

In the case of Q being equal to COOH, the procedure is performed with the methods of the malonic acid-semi-ester condensation, as described in, e.g., J. Am. Chem. Soc. 1999, 121, 7050–7062, Synth. Commun. 1997, 27, 3227–3234.

Compounds of general formula XIIIa are commercially available (e.g., Aldrich).

Compounds of general formula XIIIb are produced as described in R. C. Larock in "Comprehensive Organic Transformations," VCH Publishers New York 1989, ISBN 0-89573-710-8, pages 963–964).

In some cases, it has proven advantageous to run the diols of general formula IIa (IIa)

directly through the compounds of general formula XII (XII)

by reduction of the ester group according to the above-mentioned process.

The production of the racemic diol of general formula II can also use as starting compounds β-keto esters of general formula XIII (XIII)

according to the commonly used methods for reduction of esters and ketones.

Variant IV

For the production of optically active diols of general formula IIa, it has proven advantageous to undertake a chromatographic separation or crystallization of the diastereomeric ketals of general formulas XIVa and XIVb

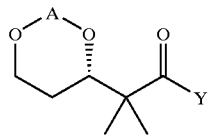
(XIVa)

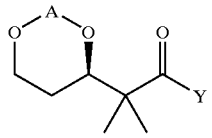
(XIVb)

in which A is taken for the radical of an optically active ketone, such as, e.g., (−) menthone, (−) camphor, etc., and then the ketal group is cleaved off according to the methods of protective group chemistry that are known to one skilled in the art.

The production of diastereomeric 1,3 diol-ketals of general formulas XIVa and XIVb is carried out from the racemic diol of general formula II by reaction with chiral ketones according to processes that are known in the literature. Lit.: T. Harada et al., J. Org. Chem. 1992, 57, 1412–1421.

Of course, the corresponding enantiomer compounds of general formula Ib

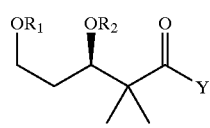
(Ib)

can also be produced with use of mirror-image catalysts or other enzyme systems.

There is also the possibility of obtaining the corresponding enantiomers in intermediate stages of general formula IIIb

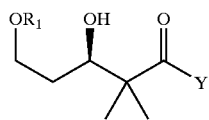
(IIIb)

by inversion of the hydroxyl group (e.g.) according to Mitsunobu (Lit.: O. Mitsunobu, Synthesis 1981, 1–28).

Of protective groups R1 and R2 that are used in the synthesis, in particular the benzyl group and the TBDMS group are preferred. In the case that R1, R2 stands for a ketal protective group, especially —(C(CH3)2)- is preferred.

Group Y can preferably stand for the radicals:

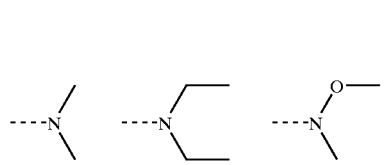 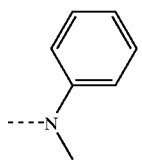 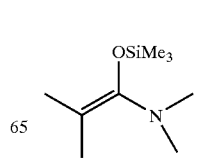 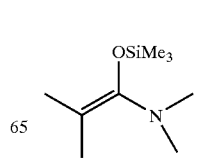

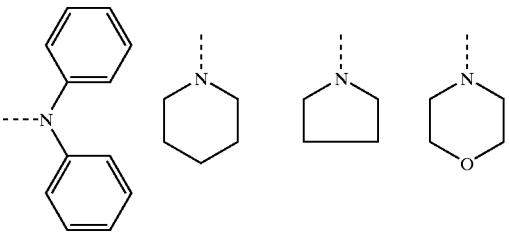

but the dimethylamino group is especially preferred.

Of the different production variants here, the following partial sequences are especially preferred for the creation of achiral precursors:

1. Production of the compounds of general formula VII from the intermediate stages of general formulas V and VIII
   L in the meaning of TMS, R1=benzyl, Nu=Cl, Y=dimethylamino

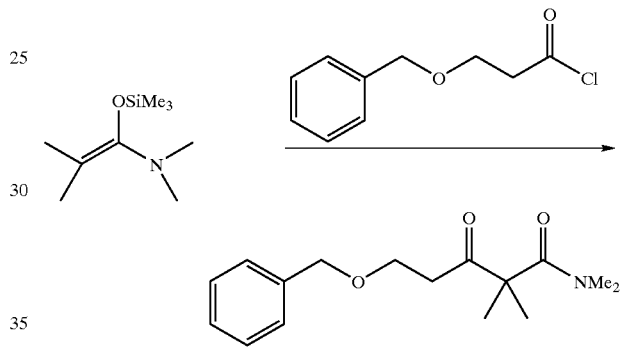

2. Production of the compounds of general formula XIII from compounds of general formulas V and XIV.
   L in the meaning of TMS, R4=ethyl, Nu=Cl, Y=dimethylamino

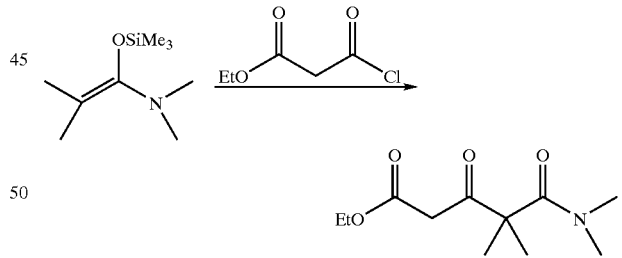

3. Production of the compounds of general formula VII by aldol condensation and subsequent oxidation
   L in the meaning of TMS, R1=benzyl, Nu=Cl, Y=dimethylamino

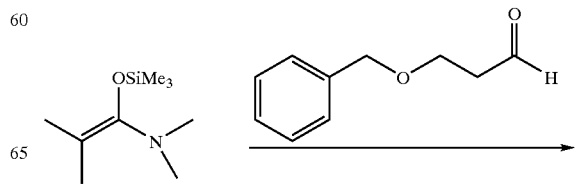

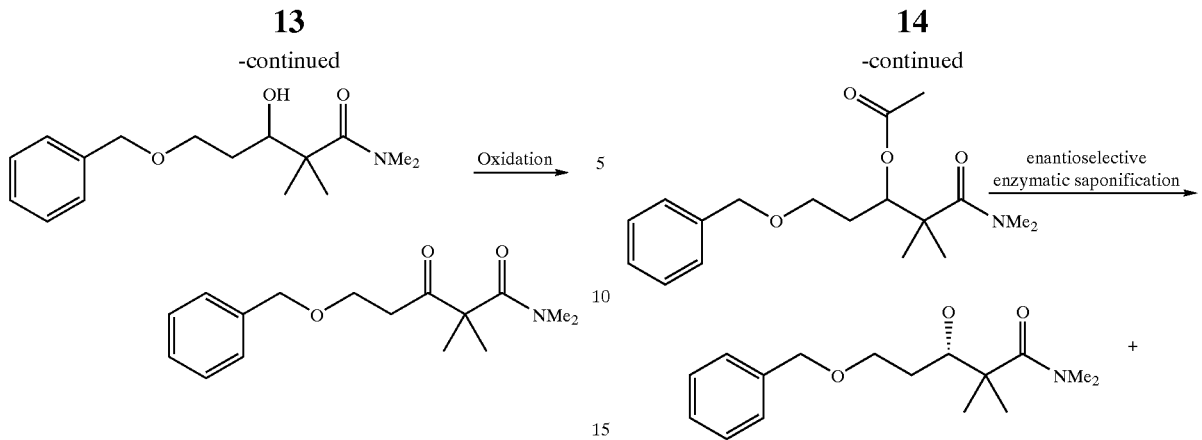

4. Production of the compounds of general formula IX (with Y=dimethylamino)

For the production of chiral precursors, especially the partial steps that are indicated below are preferred:

1. Chiral aldol condensation with a chiral catalyst

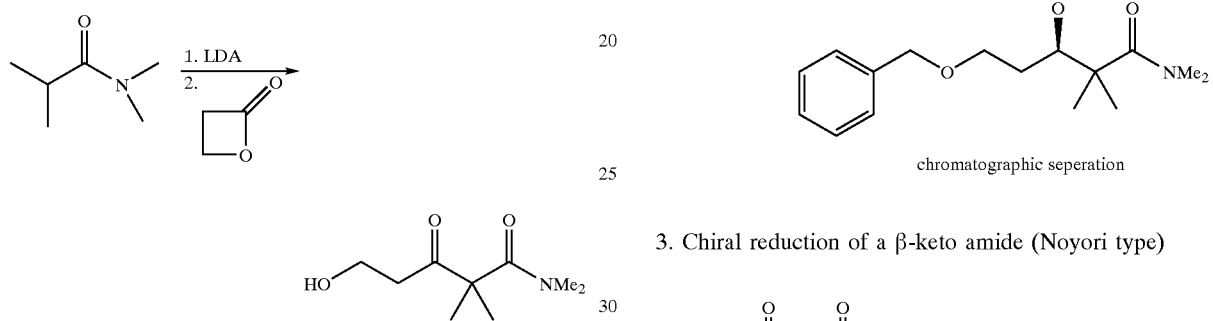

2. Enantioselective saponification of an acetate with the aid of an enzyme

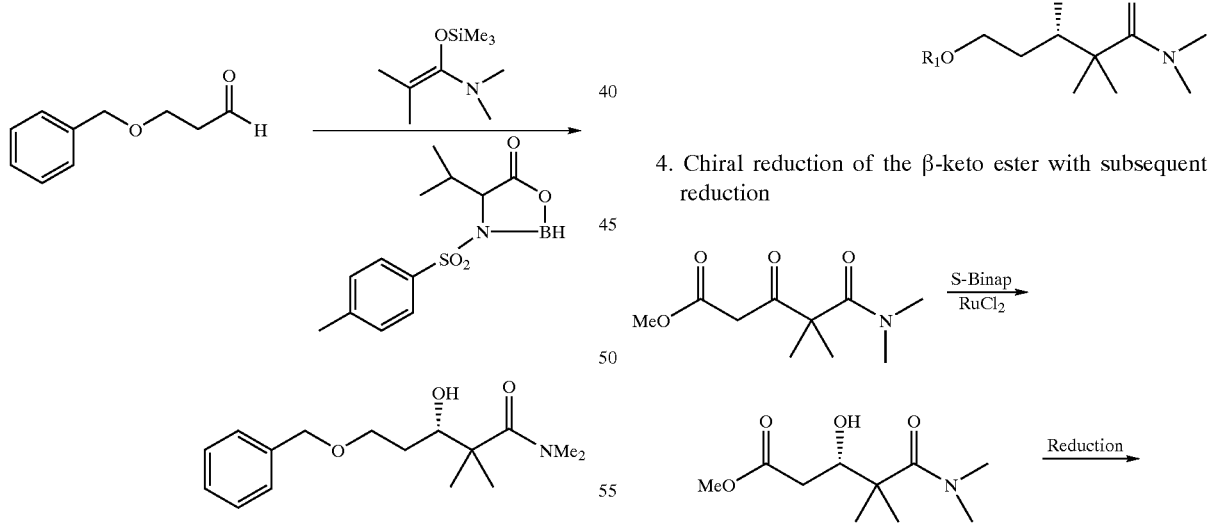

3. Chiral reduction of a β-keto amide (Noyori type)

4. Chiral reduction of the β-keto ester with subsequent reduction

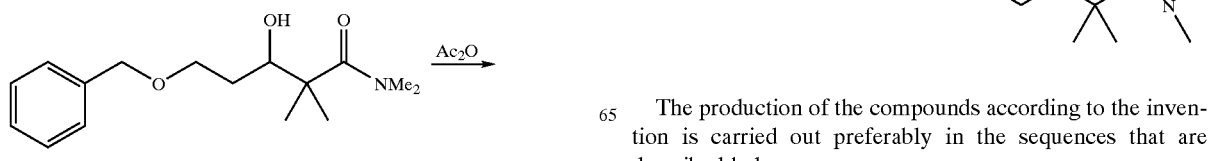

The production of the compounds according to the invention is carried out preferably in the sequences that are described below:

1. Production of acetone ketals

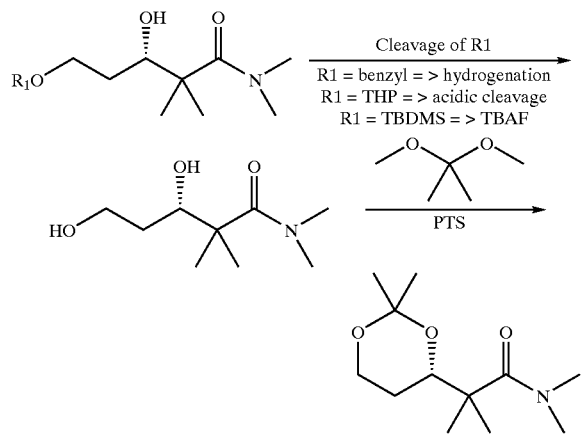

2. Production of the Di-TBDMS-protected compound

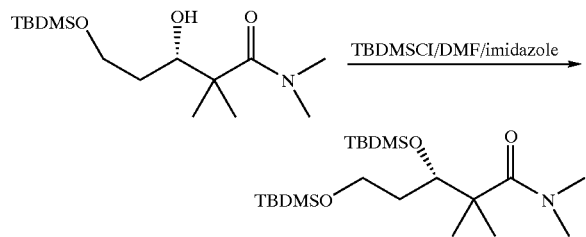

The production of the compounds and process according to the invention is to be explained in more detail in the embodiments below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1a

1-Dimethylamino-2-methyl-1-trimethylsilyl-propene 294 ml (0.45 ml) of butyllithium is added in drops at −35° C. under inert gas to 0.43 mol of diisopropylamine in 300 ml of THF. Then, 50 g (0.434 mol) of N,N-dimethyl-2-methylpropinoic acid amide is added in drops at 0° C. and stirred for 30 minutes at this temperature. Then, 60.3 ml (0.47 mol) of trimethylsilyl chloride is added at −35° C. and stirred for two more hours. The solvent is distilled off in a rotary evaporator. The residue is distilled in a vacuum at 65–69° C./30 mbar.

$^1$H-NMR (300 MHz, CDCl$_3$, 25° C., TMS), δ=0.2 (s, 9H), 1.53 (s, 3H), 1.63 (s, 3H), 2.5 (s, 6H)

| Elementary analysis: | | |
|---|---|---|
| | C | H |
| Cld. | 57.70 | 11.30 |
| Fnd. | 58.00 | 11.40 |

EXAMPLE 1b rac. N,N-Dimethyl-(5-benzyloxy-2,2-dimethyl-3(R,S)-hydroxy-pentanoic acid)amide 68.8 g (0.367 mol) of 1-dimethylamino-2-methyl-1-trimethylsilyl-propene of the title compound of Example 1a, 67 g of benzyloxy-propanol (0.4 mol) and 5.56 g>>ZnCl$_2$ are stirred in 500 ml of THF for 1 hour. 13.88 g of NH$_4$F and 300 ml of MeOH are added and stirred for 18 hours at room temperature. It is distilled off, the residue is extracted with 200 ml of ethyl acetate, and the organic phase is washed with 10% citric acid solution. After chromatography on silica gel with ethyl acetate/hexane as an eluant, 60.8 g of product is obtained (60% of theory).

| Elementary analysis: | | |
|---|---|---|
| | C | H |
| Cld. | 68.79 | 9.02 |
| Fnd. | 68.80 | 9.00 |

EXAMPLE 1c

N,N-Dimethyl-(5-benzyloxy-2,2,-dimethyl-3-oxy-pentanoic acid)amide 2.47 g of oxalyl chloride is cooled in 25 ml of methylene chloride to −60° C., 4.4 ml of DMSO in 10 ml of methylene chloride is added, and it is stirred for 15 more minutes; 7.26 g of N,N-dimethyl-(5-benzyloxy-2,2-dimethyl-3-hydroxy-pentanoic acid amide) of the title compound of Example 1b is added in 20 ml of methylene chloride, and it is stirred for 30 more minutes. 8.7 ml of triethylamine is added in drops, and it is stirred for 30 more minutes while being heated to −20° C. It is hydrolyzed with 25 ml of water, and the phase is separated. After the solvent is evaporated, 7.18 g of product is obtained. After chromatography, 3.6 g of product (50% of theory) is obtained, in addition to 1.36 g of educt.

| Elementary analysis: | | |
|---|---|---|
| | C | H |
| Cld. | 69.29 | 8.36 |
| Fnd. | 69.40 | 8.50 |

EXAMPLE 1d

N,N-Dimethyl-(5-benzyloxy-2,2,-dimethyl-3 (S)-hydroxy-pentanoic acid)amide 500 mg of N,N-dimethyl-(5-benzyloxy-2,2,-dimethyl-3-oxy-pentanoic acid)amide of the title compound of Example 1c is hydrogenated with a catalyst (produced from 23.3 mg of $RuCl_2$ $(Ph)_2$ and 62.6 mg of S.-BiNAP according to R. Selke, Angew. Chem. [Applied Chemistry] 1998, 110, 1927–1930) (2 days at 40° C./100 bar).

Yield: quantitative

| Elementary analysis: | | |
| --- | --- | --- |
| | C | H |
| Cld. | 68.79 | 9.02 |
| Fnd. | 69.00 | 9.00 |

EXAMPLE 1e

N,N-Dimethyl-3(S)-(3,5-dihydroxy-2,2,-dimethyl-pentanoic acid)amide 13.13 g (47.70 mmol) of N,N-dimethyl-(5-benzyloxy-2,2,-dimethyl-3(S)-hydroxy-pentanoic acid)amide of the title compound of Example 1d, dissolved in 110 ml of tetrahydrofuran, is added to 16 g of Pearlman's catalyst ($Pd(OH)_2$ on carbon, 20%). It is now hydrogenated for 7.5 hours at 10 bar and at room temperature. Catalyst is filtered out, and the filtrate is evaporated to the dry state in a vacuum.

Yield: 8.63 g (97% of theory) of a colorless, viscous oil.

| Elementary analysis: | | | |
| --- | --- | --- | --- |
| | C | H | N |
| Cld. | 57.12 | 10.12 | 7.40 |
| Fnd. | 57.10 | 10.00 | 7.39 |

EXAMPLE 1f

N,N-Dimethyl-(3(S)-(3,5)-Acetonedimethylketal-2,2,-dimethyl-pentanoic acid)amide 8.89 g (47 mmol) of N,N-dimethyl-(3(S)-3,5-dihydroxy-2,2,-dimethyl-pentanoic acid)amide of the title compound of Example 1e is dissolved in 27 ml of acetone dimethylketal, and 546 mg of camphor-10-sulfonic acid is added. It is heated for 15 hours to 50° C. It is evaporated to the dry state in a vacuum, the residue is taken up in 200 ml of methylene chloride and washed with saturated sodium bicarbonate solution, then with saturated sodium chloride solution. The organic phase is dried on sodium sulfate and evaporated to the dry state in a vacuum. The oil that is obtained is crystallized while standing.

Yield: 8.30 g, (77% of theory) of a colorless, crystalline solid.

| Elementary analysis: | | | |
| --- | --- | --- | --- |
| | C | H | N |
| Cld. | 62.85 | 10.11 | 6.11 |
| Fnd. | 62.90 | 10.00 | 6.00 |

EXAMPLE 1g

N,N-Dimethyl-(5-benzyloxy-2,2,-dimethyl-3(S)-hydroxy-pentanoic acid)amide 29.8 g (0.11 mol) of N-toluenesulfonyl-D-valine (Lit.: J. Am. Chem. Soc. 1937, 59, 116–118) is dissolved at 0° C. in 100 ml of dichloromethane. At 0° C., 100 ml of $BH_3$-THF solution (1 mol) is added in drops over 30 minutes and stirred for 30 more minutes. The solution is cooled to −78° C. At −78° C., 16.42 g of benzyloxy-propanal (0.1 mol) in 100 ml of dichloromethane and 22.4 g (0.12 mol) of 1-dimethylamino-2-methyl-1-trimethylsilyl-propene of the compound of Example 1a are stirred for 2 hours at −78° C. and for another 2 hours while being heated to 0° C.

5 g of $NH_4F$ and 100 ml of MeOH are added and stirred for 18 hours at room temperature. For hydrolysis, 150 ml of water is added. It is extracted with 200 ml of ethyl acetate, and the organic phase is washed with 10% citric acid solution. After chromatography on silica gel with ethyl acetate/hexane as an eluant, 24 g of product is obtained (85% of theory).

The enantiomer purity was determined by means of HPLC, stat. Phase Chiracel AD 4.6×250 mm, UV 208 nm, eluant hexane/isopropanol 99:1, flow 1 ml/min, $t_R$ (S)=75 minutes (97%), $t_R$ (R)=79 minutes (3%).

| Elementary analysis: | | |
| --- | --- | --- |
| | C | H |
| Cld. | 68.79 | 9.02 |
| Fnd. | 68.65 | 9.08 |

After a reaction to form 2-(2,2-dimethyl-[1,3]dioxan-4-yl)-2-methyl-butanon-3-one analogously to Examples 1e, 1f and 10, the enantiomer purity of compound 10 can be increased after crystallization to 99% ee.

EXAMPLE 2

N,N-Dimethyl-(3(S)-3,5-Di-tert-butyldimethylsilyloxy-2,2,-dimethyl-pentanoic acid)amide 7.13 g (104.75 mmol) of imidazole and 7.9 g (52.37 mmol) of tert-butyldimethylsilyl chloride are added to a solution that consists of 3.96 g (20.95 mmol) of N,N-dimethyl-(3(S)-3,5-dihydroxy-2,2,-dimethyl-pentanoic acid)amide of the title compound of Example 1e, in 20 ml of dimethylformamide, and it is stirred for 16 hours at room temperature. The solution is poured onto 200 ml of water and extracted twice with 50 ml each of cyclohexane. The organic phases are combined and evaporated to the dry state in a vacuum. The residue is purified by flash chromatography on silica gel (hexane/MTB-ether).

Yield: 8.31 g, (95% of theory) of a colorless, viscous oil.

Elementary analysis:

|  | C | H | N |
|---|---|---|---|
| Cld. | 60.37 | 11.34 | 3.35 |
| Fnd. | 60.40 | 11.36 | 3.29 |

EXAMPLE 3

N,N-Dimethyl-(3(S)-3,5-Cyclohexanone-dimethylketal-2,2,-dimethyl-pentanoic acid)amide 10 mg of p-toluenesulfonic acid is added to a solution that consists of 3.96 g (20.95 mmol) of N,N-dimethyl-(3(S)-3,5-dihydroxy-2,2,-dimethyl-pentanoic acid)amide of the title compound of Example 1e in 30.21 g (0.2095 mol) of cyclohexanone-dimethylketal, and it is stirred for 6 hours at 100° C. The solution is poured onto 200 ml of water and extracted twice with 50 ml each of ethyl acetate. The organic phases are combined and evaporated to the dry state in a vacuum. The residue is purified by flash chromatography on silica gel (hexane/MTB-ether).

Yield: 5.08 g (90% of theory) of a colorless, viscous oil.

Elementary analysis:

|  | C | H | N |
|---|---|---|---|
| Cld. | 68.88 | 10.10 | 5.20 |
| Fnd. | 66.90 | 10.20 | 5.21 |

EXAMPLE 4

N,N-Dimethyl-(3(S)-3,5-benzaldehyde-dimethylacetal-2,2,-dimethyl-pentanoic acid)amide 31.9 g (0.2095 mol) of benzaldehyde-dimethylacetal and 50 mg of p-toluenesulfonic acid are added to a solution that consists of 3.96 g (20.95 mmol) of N,N-dimethyl-(3(S)-3,5-dihydroxy-2,2,-dimethyl-pentanoic acid)amide of the title compound of Example 1e, in 20 ml of dimethylformamide, and it is stirred for 16 hours at 100° C. The solution is poured onto 200 ml of water and extracted twice with 50 ml each of ethyl acetate. The organic phases are combined and evaporated to the dry state in a vacuum. The residue is purified by flash chromatography on silica gel (hexane/MTB-ether).

Yield: 5.11 g (88% of theory) of a colorless, viscous oil.

Elementary analysis:

|  | C | H | N |
|---|---|---|---|
| Cld. | 69.29 | 8.36 | 5.05 |
| Fnd. | 69.30 | 8.39 | 5.00 |

EXAMPLE 5a

N,N-Dimethyl-(5-benzyloxy-2,2,-dimethyl-3(R,S)-acetoxy-pentanoic acid)amide 14.56 g (142.64 mmol) of acetic acid anhydride is added at 0° C. to a solution that consists of 30.65 g (109.7 mmol) of N,N-dimethyl-(5-benzyloxy-2,2,-dimethyl-3(R,S)-hydroxy-pentanoic acid)amide of the title compound of Example 1b, 14.43 g (142.64 mmol) of triethylamine and 200 mg of 4-dimethylaminopyridine (DMAP), dissolved in 128 ml of MTB-ether, and it is stirred for 5 hours at room temperature. It is poured onto 2 l of ice water and extracted twice with 300 ml each of MTB-ether. The combined MTB phases are washed once with 300 ml of 5% hydrochloric acid and then with water. It is evaporated to the dry state in a vacuum.

Yield: 33.50 g (95% of theory), colorless oil.

Elementary analysis:

|  | C | H | N |
|---|---|---|---|
| Cld. | 67.26 | 8.47 | 4.36 |
| Fnd. | 67.30 | 8.50 | 4.40 |

EXAMPLE 5b

N,N-Dimethyl-(5-benzyloxy-2,2,-dimethyl-3(S)-hydroxy-pentanoic acid)amide 11.67 g (36.31 mmol) of N,N-dimethyl-(5-benzyloxy-2,2,-dimethyl-3(R,S)-acetoxy-pentanoic acid)amide of the title compound of Example 5a is added to a buffer solution, produced from 0.88 g of potassium dihydrogen phosphate and 1.82 g of disodium hydrogen phosphate in 250 ml of water. Then, 5 g of the enzyme lipase AYS "Amano" (related to Amano) is added, and it is stirred for 42.5 hours at room temperature. The pH is brought to 7 by adding 2.062 g of disodium hydrogen phosphate, and then it is stirred for another 44.5 hours. Working-up: It is extracted 5 times with 400 ml of ethyl acetate. The organic phases are combined and evaporated to the dry state in a vacuum. The purification is carried out by chromatography on silica gel (hexane/ethyl acetate gradient).

Yield: 4.60 g (40% of theory) of a colorless oil.

Elementary analysis:

|  | C | H | N |
|---|---|---|---|
| Cld. | 68.79 | 9.02 | 5.01 |
| Fnd. | 68.80 | 9.00 | 5.01 |

EXAMPLE 5c

N,N-Dimethyl-(3(S)-3,5-dihydroxy-2,2,-dimethyl-pentanoic acid)amide 16 g of Pearlman's catalyst (Pd(OH)$_2$ on carbon, 20%) is added to 13.13 g (47.70 mmol) of N,N-dimethyl-(5-benzyloxy-2,2,-dimethyl-3(S)-hydroxy-pentanoic acid)amide of the title compound of Example 5b, dissolved in 110 ml of tetrahydrofuran. It is now hydrogenated for 7.5 hours at 10 bar and at room temperature. Catalyst is filtered out, and the filtrate is evaporated to the dry state in a vacuum.

Yield: 8.72 g (98% of theory) of a colorless, viscous oil.

EXAMPLE 5d

N,N-Dimethyl-(3(S)-3,5-acetonedimethylketal-2,2,-dimethyl-pentanoic acid)amide 6.62 g (35.00 mmol) of N,N-dimethyl-(3(S)-3,5-dihydroxy-2,2,-dimethyl-pentanoic acid)amide of the title compound of Example 5c is dissolved in 27 ml of acetonedimethylketal, and 546 mg of camphor-10-sulfonic acid is added. It is heated for 15 hours to 50° C. It is evaporated to the dry state in a vacuum, the residue is taken up in 200 ml of methylene chloride and washed with saturated sodium bicarbonate solution, then with saturated sodium chloride solution. The organic phase is dried on sodium sulfate and evaporated to the dry state in a vacuum. The oil that is obtained crystallizes while standing.

Yield: 5.93 g, (74% of theory) of a colorless, crystalline solid.

Elementary analysis:

|  | C | H | N |
|---|---|---|---|
| Cld. | 62.85 | 10.11 | 6.11 |
| Fnd. | 62.90 | 10.10 | 6.10 |

N-Methyl-N-phenyl-amide Synthesis

EXAMPLE 6a

1-Methyl-1-phenylamino-2-methyl-1-trimethylsilyl-propene 294 ml (0.45 ml) of butyllithium is added in drops at −35° C. under inert gas to 0.43 mol of diisopropylamine in 300 ml of THF. Then, 76.92 g (0.434 mol) of N-methyl-N-phenyl-2-methylopropionic acid amide is added in drops at 0° C. and stirred for 30 minutes at this temperature. Then, 60.3 ml (0.47 mol) of trimethylsilyl chloride is added at −35° C. and stirred for two more hours. The solvent is distilled off in a rotary evaporator. The residue is distilled in a vacuum at 65–69° C./30 mbar.

Yield: 70.36 g (65% of theory) of an oil

Elementary analysis:

|  | C | H |
|---|---|---|
| Cld. | 67.42 | 9.29 |
| Fnd. | 67.50 | 9.30 |

EXAMPLE 6b

N-Methyl-N-phenyl-(5-benzyloxy-2,2,-dimethyl-3-oxo-pentanoic acid)amide 68.8 g (0.367 mol) of 1-methyl-1-phenylamino-2-methyl-1-trimethylsilyl-propene, 81.06 g (0.401 mmol) of 3-benzyloxy-propanoic acid chloride (0.4 mol) and 5.56 g>>ZnCl$_2$ are stirred in 500 ml of THF for 1 hour. 13.88 g of NH$_4$F and 300 ml of MeOH are added and stirred for 18 hours at room temperature. It is distilled off, the residue is extracted with 200 ml of ethyl acetate, and the organic phase is washed with 10% citric acid solution. After chromatography on silica gel with ethyl acetate/hexane as an eluant, 74.74 g of product is obtained (60% of theory).

Elementary analysis:

|  | C | H |
|---|---|---|
| Cld. | 74.31 | 7.42 |
| Fnd. | 74.29 | 7.40 |

EXAMPLE 6c

N-Methyl-N-phenyl-(5-benzyloxy-2,2,-dimethyl-3(S)-hydroxy-pentanoic acid)amide 500 mg of N-methyl-N-phenyl-(5-benzyloxy-2,2,-dimethyl-3-oxo-pentanoic acid)amide of the title compound of Example 6b is hydrogenated with a catalyst (produced from 23.3 mg of RuCl$_2$ (Ph)$_2$ and 62.6 mg of S-BiNAP according to R. Selke, Angew. Chem. 1998, 110, 1927–1930) (2 days at 40° C./100 bar).

Yield: quantitative

Elementary analysis:

|  | C | H |
|---|---|---|
| Cld. | 73.87 | 7.97 |
| Fnd. | 74.00 | 8.00 |

EXAMPLE 6d

N-Methyl-N-phenyl-(3(S)-3,5-dihydroxy-2,2,-dimethyl-pentanoic acid)amide 16 g of Pearlman's catalyst (Pd(OH)$_2$ on carbon, 20%) is added [to] 16.29 g (47.70 mmol) of N-methyl-N-phenyl-(5-benzyloxy-2,2,-dimethyl-3(S)-hydroxy-pentanoic acid)amide of the title compound of Example 6c, dissolved in 110 ml of tetrahydrofuran. It is now hydrogenated for 7.5 hours at 10 bar and at room temperature. Catalyst is filtered out, and the filtrate is evaporated to the dry state in a vacuum.

Yield: 11.98 g (98% of theory) of a colorless, viscous oil.

Elementary analysis:

|  | C | H | N |
|---|---|---|---|
| Cld. | 66.91 | 8.42 | 5.57 |
| Fnd. | 66.90 | 8.40 | 5.60 |

EXAMPLE 6e

N-Methyl-N-phenyl-(3(S)-(3,5)-acetonedimethylketal-2,2,-dimethyl-pentanoic acid)amide 11.81 g (47 mmol) of N-methyl-N-phenyl-(3(S)-3,5-dihydroxy-2,2,-dimethyl-pentanoic acid)amide of the title

---

Elementary analysis:

|  | C | H | N |
|---|---|---|---|
| Cld. | 57.12 | 10.12 | 7.40 |
| Fnd. | 57.10 | 10.10 | 7.39 | compound of Example 6d is dissolved in 27 ml of acetonedimethylketal, and 546 mg of camphor-10-sulfonic acid is added. It is heated for 15 hours to 50° C. It is evaporated to the dry state in a vacuum, the residue is taken up in 200 ml of methylene chloride and washed with saturated sodium bicarbonate solution, then with saturated sodium chloride solution. The organic phase is dried on sodium sulfate and evaporated to the dry state in a vacuum. The oil that is obtained crystallizes while standing.

Yield: 10.54 g, (77% of theory) of a colorless, crystalline solid.

Elementary analysis:

|  | C | H | N |
|---|---|---|---|
| Cld. | 70.07 | 8.65 | 4.81 |
| Fnd. | 70.00 | 8.50 | 4.90 |

EXAMPLE 7

N-Methyl-N-phenyl-(3(S)-3,5-cyclopentanonedimethylketal-2,2,-dimethyl-pentanoic acid)amide 10 mg of p-toluenesulfonic acid is added to a solution that consists of 5.26 g (20.95 mmol) of N-methyl-N-phenyl-(3(S)-3,5-dihydroxy-2,2,-dimethyl-pentanoic acid)amide of the title compound of Example 6d) in 30.21 g (0.2095 mol) of cyclopentanone-dimethylketal, and it is stirred for 6 hours at 100° C. The solution is poured onto 200 ml of water and extracted twice with 50 ml each of ethyl acetate. The organic phases are combined and evaporated to the dry state in a vacuum. The residue is purified by flash chromatography on silica gel (hexane/MTB-ether).

Yield: 5.98 g (90% of theory) of a colorless, viscous oil.

Elementary analysis:

|  | C | H | N |
|---|---|---|---|
| Cld. | 71.89 | 8.57 | 4.41 |
| Fnd. | 71.90 | 8.60 | 4.50 |

EXAMPLE 8

N-Methyl-N-phenyl-(3(S)-3,5-dichlorodiphenylsilane-2,2,-dimethyl-pentanoic acid)amide 3.14 g (46.09 mmol) of imidazole and 5.83 g (23.05 mmol) of dichlorodiphenylsilane are added to a solution that consists of 5.26 g (20.95 mmol) of N-methyl-N-phenyl-(3(S)-3,5-dihydroxy-2,2,-dimethyl-pentanoic acid)amide of the title compound of Example 6d, in 20 ml of dimethylformamide, and it is stirred for 16 hours at room temperature. The solution is poured onto 200 ml of water and extracted twice with 50 ml each of methylene chloride. The organic phases are combined and evaporated to the dry state in a vacuum. The residue is purified by flash chromatography on silica gel (hexane/MTB-ether).

Yield: 7.68 g (85% of theory) of a colorless, viscous oil.

Elementary analysis:

|  | C | H | N |
|---|---|---|---|
| Cld. | 72.35 | 6.77 | 3.25 |
| Fnd. | 72.37 | 6.80 | 3.30 |

EXAMPLE 9a rac. N,N-Dimethyl-(3-hydroxy-3-oxo-pentanoic acid)amide 13 ml (26 mmol) of a 2 mol LDA-THF solution is added at −50° C. to 2.99 g (26 mmol) of N,N-dimethyl-2-methylpropinonic acid amide and stirred for 30 minutes at this temperature. Then, 1.44 g (20 mmol) of propiolactone is added, and it is stirred for 20 more hours while being heated to room temperature. It is hydrolyzed with saturated ammonium chloride solution and extracted with ethyl acetate. After drying at 1 mbar, 2.8 g of Example 9a (77% of theory) is obtained.

Elementary analysis:

|  | C | H | N |
|---|---|---|---|
| Cld. | 57.72 | 9.15 | 7.47 |
| Fnd. | 58.05 | 8.95 | 7.75 |

EXAMPLE 9b

N,N-Dimethyl-3(S)-(3,5-dihydroxy-2,2,-dimethyl-pentanoic acid)amide 1.87 g (10 mmol) of rac. N,N-dimethyl-(3-hydroxy-3-oxo-pentanoic acid)amide of the title compound of Example 1c is hydrogenated with a catalyst (produced from 75 mg of $RuCl_2 (Ph)_2$ and 190 mg of S-BiNAP according to R. Selke, Angew. Chem. 1998, 110, 1927–1930) (2 days at 40° C./100 bar).

Yield: quantitative

Elementary analysis:

|  | C | H | N |
|---|---|---|---|
| Cld. | 57.11 | 10.1 | 7.4 |
| Fnd. | 57.60 | 10.3 | 7.7 |

EXAMPLE 10

(S)-3-(2,2-Dimethyl-[1,3]dioxan-4-yl)-3-methyl-butan-2-one 35.6 ml of methyllithium-lithium bromide complex (1.5 M in diethyl ether) is added in drops at −20° C. to 4.08 g (17.79 mmol) of the title compound of Example 1f, N,N-dimethyl-(3(S)-3,5-acetonedimethylketal-2,2,-dimethyl-pentanoic acid)amide, dissolved in 5 ml of diethyl ether.

Then, it is stirred for 30 minutes at −20° C. and then heated to room temperature. It is stirred overnight at room temperature. 10 ml of saturated ammonium chloride solution is added, and it is stirred for 6 hours at room temperature. The organic phase is separated and washed twice with water. The organic phase is evaporated to the dry state in a vacuum. The purification is carried out by chromatography on silica gel (hexane/ethyl acetate gradient).

Yield: 2.77 g (78% of theory) of an oil.

Elementary analysis:

|  | C | H |
|---|---|---|
| Cld. | 65.97 | 10.07 |
| Fnd. | 65.84 | 10.19 |

EXAMPLE 11

(S)-2-(2,2-Dimethyl-[1,3]dioxan-4-yl)-2-methyl-heptan-3-one 34 ml of n-butyllithium 15% (1.6 M in hexane) is added in drops at −65° C. to 4.08 g (17.79 mmol) of the title compound of Example 1f, N,N-dimethyl-(3(S)-3,5-acetonedimethylketal-2,2,-dimethyl-pentanoic acid)amide, dissolved in 5 ml of THF. Then, it is stirred for 5 hours at −65° C. and then heated to room temperature. It is stirred overnight at room temperature. 10 ml of saturated ammonium chloride solution is added, and it is stirred for 6 hours at room temperature. The organic phase is separated and washed twice with water. The organic phase is evaporated to the dry state in a vacuum. The purification is carried out by chromatography on silica gel (hexane/ethyl acetate gradient).

Yield: 4.13 g (96% of theory) of an oil.

Elementary analysis:

|  | C | H |
|---|---|---|
| Cld. | 69.38 | 10.81 |
| Fnd. | 69.27 | 10.96 |

EXAMPLE 12

(4S)-4-(2-Methyl-3-oxo-hept-6-en-2-yl)-2,2-dimethyl-[1,3] dioxane 50 ml of 3-butenyllithium solution (produced from 4-bromo-1-butene and lithium wire or tert-butyllithium, according to J. Org. Chem. Vol. 56, No. 21, pp. 6094–6103 (1991) or J. Chem. Soc. Perkin Trans. 1 pp. 2937, (1988)) is added in drops at −90° C. to 4.08 g (17.79 mmol) of the title compound of Example 1 f, N,N-dimethyl-(3(S)-3,5-acetonedimethylketal-2,2,-dimethyl-pentanoic acid)amide, dissolved in 5 ml of diethyl ether. Then, it is stirred for 17 hours at −90° C. and then heated to room temperature. It is stirred overnight at room temperature for 17 hours. 10 ml of saturated ammonium chloride solution is added, and it is stirred for 6 hours at room temperature. The organic phase is separated and washed twice with water. The organic phase is evaporated to the dry state in a vacuum. The purification is carried out by chromatography on silica gel (hexane/ethyl acetate gradient).

Yield: 2.74 g (70% of theory) of a colorless oil

Elementary analysis:

|  | C | H |
|---|---|---|
| Cld. | 69.96 | 10.06 |
| Fnd. | 69.90 | 10.05 |

EXAMPLE 13

N,N-Dimethyl-2,2-dimethyl-pentane-1,5-dicarboxylic acid-1-amide-5-ethyl ester 0.81 g (5.35 mmol) of malonic acid monoethyl ester chloride is added at 0° C. to 1 g of 1-dimethylamino-2-methyl-1-trimethylsilyl-propene (5.35 mmol); 72 mg of anhydrous ZnCl2 is subsequently added as catalyst, and it is stirred for 2 hours at 0° C. It is added to 10 ml of water, chromatographed twice with 10 ml each of ethyl acetate and chromatographed on silica gel.

Yield: 0.958 g (77% of theory).

MS-CI/NH$_3$ (70 eV), M/Z=230 [M−H]$^+$ $^1$H-NMR (300 MHz, CDCl$_3$, 25° C., TMS) δ=01.4 (s, 6H), 2.9 (m, 6H), 3.48 (s, 2H), 4.25 (m, 4H)

Abbreviations of the Ether Protective Groups that are Used:
TES=Triethylsilyl
TMS=Trimethylsilyl
TIP=Triisopropyl
TBDPS tert-Butyl-dimethylsilyl
MEM=Methylethoxymethyl
MOM=Methyloxymethyl
THP=Tetrahydropyranyl-(ether)

Abbreviations of the Ether Protective Groups that are Used:
TES=Triethylsilyl
TMS=Trimethylsilyl
TIP=Triisopropyl
TBDPS=tert-Butyl-dimethylsilyl
MEM=Methylethoxymethyl
MOM=Methyloxymethyl
THP=Tetrahydropyranyl-(ether)

The entire disclosures of all applications, patents and publications, cited herein and of corresponding German application No. 101 38 348.7, filed Aug. 3, 2001, and U.S. Provisional Application Ser. No. 60/313,015, filed Aug. 20, 2001, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula I:

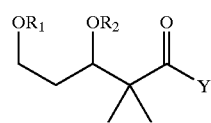

in which

R₁ and R₂ are the same or different and, independently of one another, stand for an alcohol protective group or, R₁ and R₂ are bridged and together stand for a ketal protective group, and Y stands for a group -NA1A2, whereby A1 and A2, independently of one another, stand for $C_1$–$C_6$ alkyl, aryl, aralkyl, —OH, —OMe, or —O-benzyl, or Y stands for

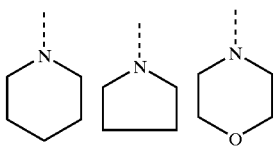

where the dashed line bonds indicate the point of attachment.

2. A compound of claim 1, wherein the alcohol protective groups are selected from: benzyl, 4-methoxybenzyl, 3,4-dimethoxybenzyl, THP, TBDMS, TMS, TES, TIP, TBDPS, MEM, MOM, allyl and trityl groups; and the ketal protective group is selected from groups of the following formulae:

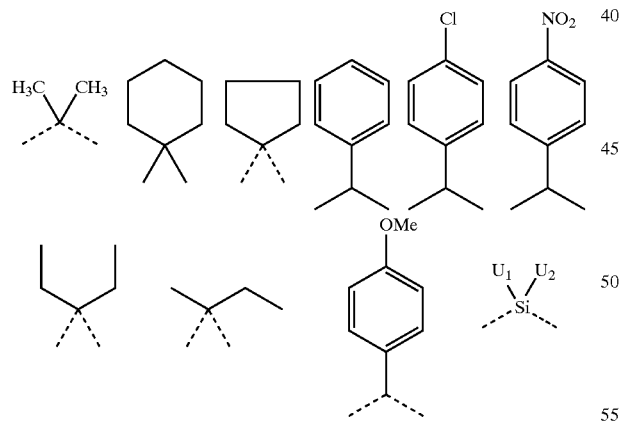

where the dashed line bonds indicate the points of attachment.

3. A compound of claim 1, wherein for A1 and A2, aryl is phenyl and aralkyl is benzyl.

4. A compound of claim 1, which is of the formula Ia:

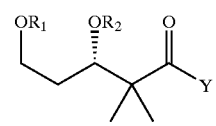

in which R₁, R₂ and Y have the meanings given in claim 1.

5. A compound of claim 1, which is of the formula Ib:

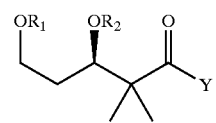

in which R₁, R₂ and Y have the meanings given in claim 1.

6. A compound of claim 4, which is N,N-dimethyl-(3(S)-(3,5)-acetonedimethylketal-2,2,-dimethyl-pentanoic acid) amide of the formula:

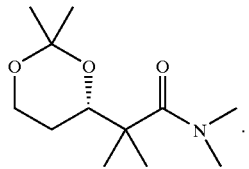

7. A compound of claim 4, which is N,N-dimethyl-(3(S)-3,5-benzaldehyde-dimethylacetal-2,2-dimethyl-pentanoic acid)amide of the formula:

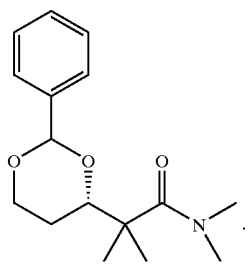

8. A compound of claim 4, which is N,N-dimethyl-(3(S)-3,5-di-tert-butyldimethylsilyloxy-2,2,-dimethyl-pentanoic acid)amide of the formula:

9. A compound of claim 4, which is N,N-dimethyl-(3(S)-3,5-cyclohexanone-dimethylketal-2,2,-dimethyl-pentanoic acid)amide of the formula:

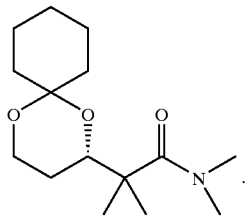

10. A compound of claim 4, which is N-methyl-N-phenyl-(3(S)-(3,5)-acetonedimethylketal-2,2,-dimethyl-pentanoic acid)amide of the formula:

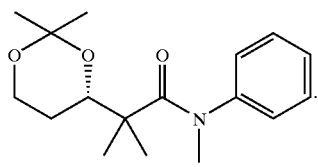

11. A compound of claim 4, which is N-methyl-N-phenyl-(3(S)-3,5-cyclopentanonedimethylketal-2,2,-dimethyl-pentanoic acid)amide of the formula:

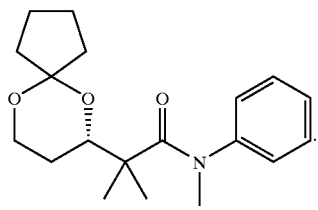

12. A compound of claim 4, which is N-methyl-N-phenyl-(3(S)-3,5-diphenylsilanoxy-2,2,-dimethyl-pentanoic acid)amide of the formula:

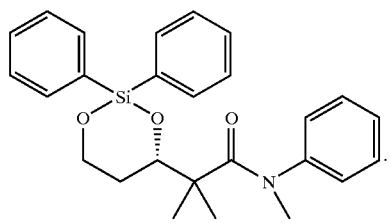

13. A compound of formula II:

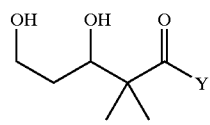
(II)

in which Y stands for a group -NA1A2, where A1 and A2, independently of one another, stand for $C_1$–$C_6$ alkyl, aryl, aralkyl, —OH, —OMe, or —O-benzyl, or Y is

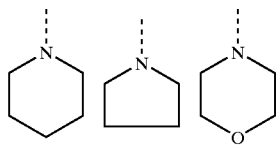

where the dashed line bonds indicate the point of attachment.

14. A compound of claim 13, wherein the configuration at the C-atom of the secondary alcohol is S.

15. A compound of claim 13, wherein the configuration at the C-atom of the secondary alcohol is R.

16. A compound of claim 13, wherein for A1 and A2, aryl is phenyl and aralkyl is benzyl.

17. A compound of claim 13, which is N,N-dimethyl-(3 (S)-(3,5-dihydroxy-2,2,-dimethyl-pentanoic acid)amide of the formula:

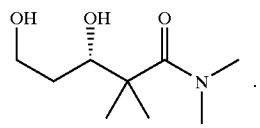

18. A compound of formula III:

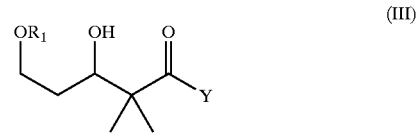
(III)

in which

R$_1$ stands for an alcohol protective group, and

Y stands for a group -NA1A2, where A1 and A2, independently of one another, stand for $C_1$–$C_6$ alkyl, aryl, aralkyl, —OH —OMe or —O-benzyl, or Y is

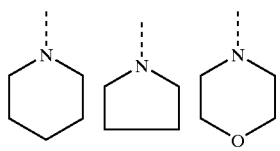

where the dashed line bonds indicate the point of attachment.

19. A compound of claim 18, wherein the alcohol protective group is selected from: benzyl, 4-methoxybenzyl, 3,4-dimethoxybenzyl, THP, TBDMS, TMS, TES, TIP, TBDPS, MEM, MOM, allyl and trityl groups.

20. A compound of claim 18, wherein for A1 and A2, aryl is phenyl and aralkyl is benzyl.

21. A compound of claim 18, wherein the configuration at the C-atom of the secondary alcohol is S.

22. A compound of claim 18, wherein the configuration at the C-atom of the secondary alcohol is R.

* * * * *